(12) United States Patent
Olson

(10) Patent No.: US 11,707,312 B2
(45) Date of Patent: Jul. 25, 2023

(54) APPARATUSES AND METHODS FOR COOLING TISSUE OR FLUID

(71) Applicant: St. Jude Medical, Cardiology Division, Inc., St. Paul, MN (US)

(72) Inventor: Gregory K. Olson, Elk River, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 759 days.

(21) Appl. No.: 16/624,235

(22) PCT Filed: Jun. 18, 2018

(86) PCT No.: PCT/US2018/038090
§ 371 (c)(1),
(2) Date: Dec. 18, 2019

(87) PCT Pub. No.: WO2018/236757
PCT Pub. Date: Dec. 27, 2018

(65) Prior Publication Data
US 2020/0129219 A1 Apr. 30, 2020

Related U.S. Application Data

(60) Provisional application No. 62/521,992, filed on Jun. 19, 2017.

(51) Int. Cl.
*A61B 18/00* (2006.01)
*A61M 3/02* (2006.01)
*A61B 18/14* (2006.01)

(52) U.S. Cl.
CPC .......... *A61B 18/00* (2013.01); *A61M 3/0279* (2013.01); *A61B 18/1492* (2013.01);
(Continued)

(58) Field of Classification Search
CPC ................ A61B 18/00; A61B 18/1492; A61B 2018/00047; A61B 2018/00375;
(Continued)

(56) References Cited

U.S. PATENT DOCUMENTS

2001/0005791 A1* 6/2001 Ginsburg .............. A61F 7/0097
607/113
2007/0027449 A1 2/2007 Godara et al.
(Continued)

FOREIGN PATENT DOCUMENTS

KR 10-2015-0031324 A 3/2015

*Primary Examiner* — Aaron F Roane
(74) *Attorney, Agent, or Firm* — Armstrong Teasdale LLP

(57) ABSTRACT

An apparatus for cooling tissue or a fluid for an elongate medical device comprising an elongate shaft extending along a longitudinal axis and comprising a shaft proximal end and a shaft distal end; a support structure located at the shaft distal end, where the support structure is expandable from a contracted state to an expanded state, and a plurality of thermoelectric elements, wherein the thermoelectric elements are located on the support structure. A medical device comprising a first catheter end shape, a second catheter end shape located distally with respect to the first catheter end shape, a support structure that extends between the first and the second catheter end shape, and a plurality of thermoelectric elements. A system for cooling a tissue or a fluid for an elongate medical device, comprising a plurality of thermoelectric elements, a thermocouple, an electronic control unit (ECU).

29 Claims, 11 Drawing Sheets

(52) U.S. Cl.
CPC .............. *A61B 2018/00047* (2013.01); *A61B 2018/00375* (2013.01); *A61B 2018/00577* (2013.01); *A61M 2205/3606* (2013.01); *A61M 2205/3673* (2013.01)

(58) Field of Classification Search
CPC ...... A61B 2018/00577; A61M 3/0279; A61M 2205/3606; A61M 2205/3673
USPC ........................................................ 604/114
See application file for complete search history.

(56) References Cited

U.S. PATENT DOCUMENTS

| | | | |
|---|---|---|---|
| 2007/0129720 A1* | 6/2007 | Demarais | A61N 1/36007 606/41 |
| 2008/0161890 A1 | 7/2008 | Lafontaine | |
| 2015/0223704 A1 | 8/2015 | Haverkost et al. | |
| 2016/0022966 A1* | 1/2016 | Chuter | A61M 25/104 29/428 |
| 2017/0143403 A1 | 5/2017 | Nau et al. | |
| 2018/0008332 A1* | 1/2018 | Sheth | A61B 18/02 |

\* cited by examiner

APPARATUSES AND METHODS FOR COOLING TISSUE OR FLUID

CROSS-REFERENCE TO RELATED APPLICATIONS

This application claims the benefit of U.S. provisional application No. 62/521,992, filed 19 Jun. 2017, which is hereby incorporated by reference as though fully set forth herein.

BACKGROUND a. Field

This disclosure relates to apparatuses and methods for cooling a tissue or a fluid. In particular, the instant disclosure relates to using a thermoelectric element to cool a tissue or a fluid.

b. Background Art

Electrophysiology catheters are used in a variety of diagnostic and/or therapeutic medical procedures to correct conditions such as atrial arrhythmia, including for example, ectopic atrial tachycardia, atrial fibrillation, and atrial flutter. Arrhythmia can create a variety of dangerous conditions including irregular heart rates, loss of synchronous atrioventricular contractions and stasis of blood flow which can lead to a variety of ailments and even death.

In a typical procedure, a catheter is manipulated through a patient's vasculature to, for example, a patient's heart, and carries one or more electrodes which may be used for diagnosis, mapping, ablation, or other treatments. Once at the intended site, treatment may involve radio frequency (RF) ablation, cryoablation, lasers, chemicals, high-intensity focused ultrasound, etc. An ablation catheter imparts such ablative energy to cardiac tissue to create a lesion in the cardiac tissue. This lesion disrupts undesirable electrical pathways and thereby limits or prevents stray electrical signals that lead to arrhythmias. As readily apparent, such treatment requires precise control of the catheter during manipulation to and at the treatment site, which can invariably be a function of a user's skill level.

Prior practice for delivering multiple ablations to tissue involves making a first ablation at a single point a n ablation catheter, then moving the ablation catheter on to the second ablation at a second point, and then moving to ablation catheter to the third site and so on. The single point ablations are made, often adjacent to one another, creation a lesion line. A frequent location for ablation lines are around/between the pulmonary veins in the left atrium of the heart. There are devices in development or being commercialized that attempt to achieve a sufficient block of ablations with minimal applications of energy. These are typically referred to as "one-shot-PVI" (pulmonary vein isolation) devices. Existing designs range from diagnostic catheters with a hoop and balloon mounted designs with features to apply energy. Existing designs are challenged when it comes to maintaining consistent contact between the tissue/vessel and all of the electrodes.

The delivery of ablations to an area of tissue often generates heat (e.g., RF ablation). A buildup of heat from ablations can cause the blood passing by an ablation site to absorb the heat which can cause an increase in the temperature of the blood. Excessive blood temperatures can be detrimental to the blood constituents and the physiological characteristics of the blood.

BRIEF SUMMARY

The instant disclosure, in at least one embodiment, an apparatus for cooling a tissue or a fluid comprises an elongate shaft extending along a longitudinal axis and comprising a proximal portion and a distal portion. The distal portion of the elongate shaft can include a support structure, where the support structure is expandable from a contracted state to an expanded state. The medical device also comprises a thermoelectric element, where the thermoelectric element is located on the support structure.

In another embodiment, an apparatus comprises a first shaping element configured to have an expanded state and a contracted state, a second shaping element located distally with respect to the first shaping element and configured to have an expanded state and a contracted state, wherein each of the first and the second shaping elements are transversely oriented when each is in the expanded state with respect to a longitudinal axis that extends through a center of each shaping element. The apparatus also comprises a support structure that extends between the first shaping element and the second shaping element and a thermoelectric element, wherein the thermoelectric element is located on the support structure.

In yet another embodiment, a system for cooling a tissue or a fluid comprises a plurality of thermoelectric elements, a thermocouple, an electronic control unit (ECU). The ECU is configured to measure a first temperature at a location, apply power to a plurality off thermoelectric elements, and measure a second temperature at the location.

In another embodiment, an apparatus for an elongate medical device comprises a flexible planar substrate, a plurality of thermoelectric elements, where the plurality of thermoelectric elements are arranged in a first pattern on the flexible planar substrate, and a plurality of interactive elements, wherein the interactive elements are arranged in a second pattern on the flexible planar substrate.

DETAILED DESCRIPTION OF EMBODIMENTS

Figure 1:
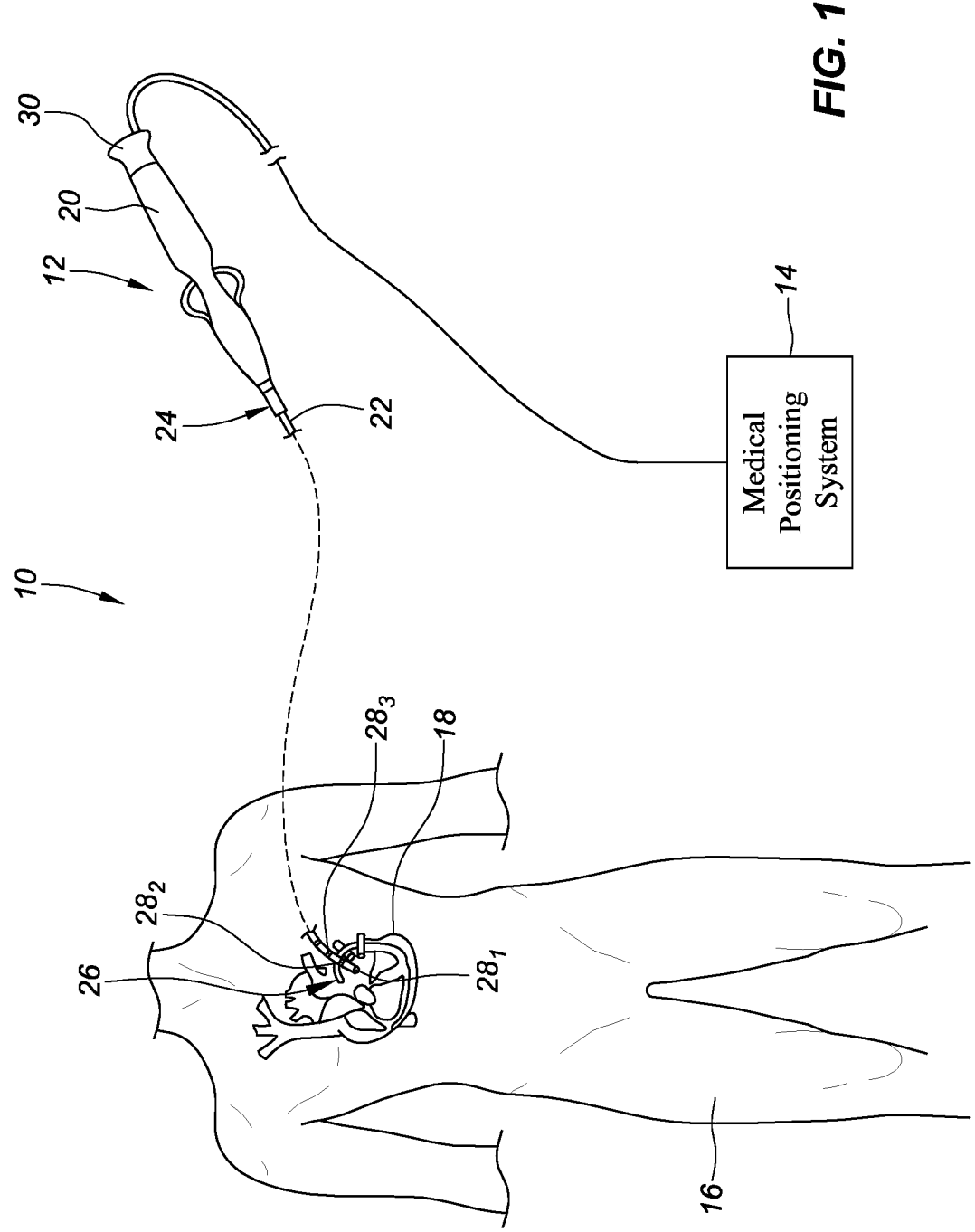
FIG. 1 is a system diagram showing a medical device and a medical positioning system, in accordance with embodiments of the present disclosure.

FIG. 1 is a system diagram showing a medical device and a medical positioning system, in accordance with embodiments of the present disclosure. In some embodiments, and with reference to FIG. 1, the system 10 can include a medical device 12 and a medical positioning system 14. The medical device 12 can include an elongate medical device such as, for example and without limitation, a catheter, or a sheath, introducer, endoscope, or other device configured for insertion into the body. For purposes of illustration and clarity, the description below will be limited to an embodiment wherein the medical device 12 comprises a catheter (a sample catheter is shown in FIG. 1 (e.g., catheter 12). It will be appreciated, however, that the present disclosure is not meant to be limited to catheters.

With continued reference to FIG. 1, the catheter 12 can be configured to be inserted into a patient's body 16, and more particularly, into the patient's heart 18. The catheter 12 may include a handle 20 that has a proximal end 30, a shaft 22 having a proximal end portion 24 and a distal end portion 26, and one or more sensors 28 mounted in or on the shaft 22 of the catheter 12. As used herein, "sensor 28" or "sensors 28" may refer to one or more sensors $28_1$, $28_2$, $28_3$ ... $28_N$, as appropriate and as generally depicted. In an exemplary embodiment, the sensors 28 are disposed at the distal end portion 26 of the shaft 22. The catheter 12 may further include other conventional components such as, for example and without limitation, a temperature sensor, additional sensors or electrodes, ablation elements (e.g., ablation tip electrodes for delivering RF ablative energy, high intensity focused ultrasound ablation elements, etc.), and corresponding conductors or leads.

The shaft 22 can be an elongate, tubular, flexible member configured for movement within the body 16. The shaft 22 supports, for example and without limitation, sensors and/or electrodes mounted thereon, such as, for example, the sensors 28, associated conductors, and possibly additional electronics used for signal processing and conditioning. The shaft 22 may also permit transport, delivery, and/or removal of fluids (including irrigation fluids, cryogenic ablation fluids, and bodily fluids), medicines, and/or surgical tools or instruments. The shaft 22 may be made from conventional materials such as polyurethane, and define one or more lumens configured to house and/or transport electrical conductors, fluids, or surgical tools. The shaft 22 may be introduced into a blood vessel or other structure within the body 16 through a conventional introducer. The shaft 22 may then be steered or guided through the body 16 to a desired location, such as the heart 18.

The sensors 28 mounted in or on the shaft 22 of the catheter 12 may be provided for a variety of diagnostic and therapeutic purposes including, for example and without limitation, electrophysiological studies, pacing, cardiac mapping, and ablation. In an exemplary embodiment, one or more of the sensors 28 are provided to perform a location or position sensing function. More particularly, and as will be described in greater detail below, one or more of the sensors 28 are configured to be a positioning sensor that provides information relating to the location (e.g., position and orientation) of the catheter 12, and the distal end portion 26 of the shaft 22 thereof, in particular, at certain points in time. Accordingly, in such an embodiment, as the catheter 12 is moved along a surface of a structure of interest of the heart 18 and/or about the interior of the structure, the sensor(s) 28 can be used to collect location data points that correspond to the surface of, and/or other locations within, the structure of interest. These location data points can then be used for a number of purposes such as, for example and without limitation, the construction of surface models of the structure of interest.

For purposes of clarity and illustration, the description below will be with respect to an embodiment wherein a single sensor 28 of the catheter 12 comprises a positioning sensor. It will be appreciated, however, that in other exemplary embodiments, which remain within the spirit and scope of the present disclosure, the catheter 12 may comprise more than one positioning sensor as well as other sensors or electrodes configured to perform other diagnostic and/or therapeutic functions. As will be described in greater detail below, the sensor 28 can include a pair of leads extending from a sensing element thereof (e.g., a coil) that are configured to electrically couple the sensor 28 to other components of the system 10, such as, for example, the medical positioning system 14. In some embodiments, the sensing element can be an electromagnetic position sensor, such as a sensor coil, which can sense a magnetic field that is generated in proximity to the patient. Depending on a position and orientation (P&O) of the electromagnetic position sensor, different electrical signals can be generated by the coil and transferred to the medical positioning system, for a determination of a location reading that can be indicative of the P&O of the electromagnetic position sensor.

The location readings may each include at least one or both of a position and an orientation (P&O) relative to a reference coordinate system, which may be the coordinate system of medical positioning system 14. For some types of sensors, the P&O may be expressed with five degrees-of-freedom (five DOF) as a three-dimensional (3D) position a coordinate in three axes X, Y and Z) and two-dimensional (2D) orientation (e.g., an azimuth and elevation) of sensor 28 in a magnetic field relative to a magnetic field generator(s) or transmitter(s) and/or a plurality of electrodes in an applied electrical field relative to an electrical field generator (e.g., a set of electrode patches). For other sensor types, the P&O may be expressed with six degrees-of-freedom (six DOF) as a 3D position (i.e., X, Y, Z coordinates) and 3D orientation (i.e., roll, pitch, and yaw).

Applying ablation energy to tissue can add heat to the surrounding blood. For example, ablating tissue in the Pulmonary Vein (PV) during PV isolation (PVI) can heat the blood as it passes through the PV. A typical baseline blood temperature can be 37° C. Heating the blood can have negative effects (e.g., denaturation of proteins). Literature suggests that 40° C. is a safe temperature and that 42° C. is possibly safe. Higher temperatures can have a negative effect on the blood.

Heat can be dissipated from blood at a certain rate. For example, the thermodilution of blood can be $$\frac{dH}{dt} = \rho_b c_{Pb}(T(t) - T_b)\frac{dV}{dt}$$

Where $\rho_b$ = blood density (approximately 1050 kg/m ∧ 3

$c_{Pb}$ = heat capacity (approximately 3594 J/kg° C $\frac{dH}{dt}$ = heat input from device $T(t)$ = current temperature of the blood (°C.)

$T_b$ = baseline blood temperature (appromimately 37° C.)

$\frac{dV}{dt}$ = blood flow rate (appromimately 5 l/min

For example, with a blood temperature of 40° C., plugging in the values above yields a $$42° C. \frac{dH}{dt}$$

For a blood temperature of $\frac{dH}{dt}$ of 943 J/s.

increases to 1572 J/s.

Thermoelectric cooling uses the Peltier effect to create heat flux between the junction of two different types of materials A Peltier cooler, heater or thermoelectric heat pump is a solid-state active heat pump which transfers heat from one side of the device to the other, with consumption of electrical energy, depending on the direction of the current. Such an instrument is also called a Peltier device, Peltier heat pump, solid state refrigerator, or thermoelectric cooler. A thermoelectric cooler can be used either for heating or cooling. A thermoelectric cooler can also be used as a temperature controller that either heats or cools. Thermoelectric cooling can be a useful tool for cooling or heating a tissue or a liquid (e.g., blood) during medical procedures such as ablation.

Figure 2:
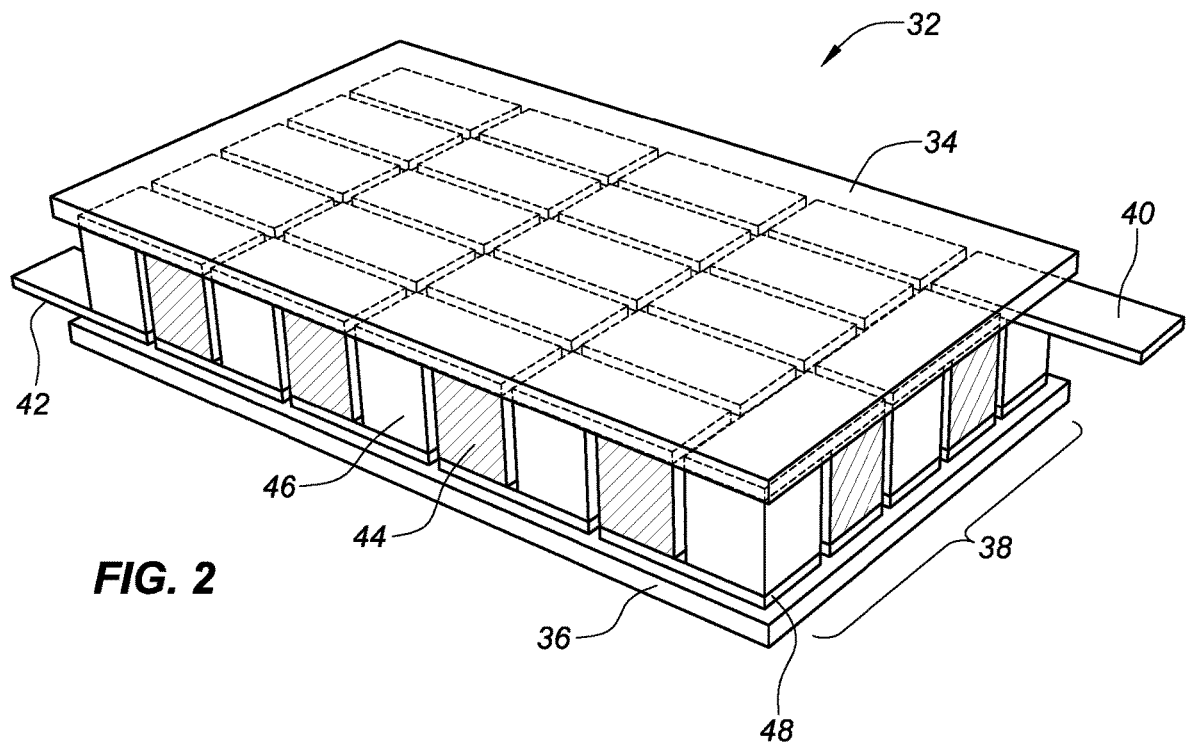
FIG. 2 is a isometric side and top view of a thermoelectric circuit (TEC), in accordance with embodiments of the present disclosure.

FIG. 2 is a isometric side and top view of a thermoelectric circuit (TEC), in accordance with embodiments of the present disclosure. The TEC 32 can include a top plate 34, a bottom plate 36, a plurality of semiconductors 38, a first electrical connection 40 and a second electrical connection 42. The plurality of semiconductors 38 can be located in between the top plate 34 and the bottom plate 36.

The top plate 34 and the bottom plate 36 can be made from a material that is thermally conductive (e.g., metal, polymers that include conductive properties or coatings, metal matrix composites, etc.). The top plate 34 and bottom plate 36 can be the same material or they can be different materials. For example, the top plate 34 and the bottom plate 36 can be a ceramic material. The plurality of semiconductors 38 can include a first semiconductor 44 and a second semiconductor 46. The first semiconductor 44 can be, for example, an n-type and the second semiconductor 46 can be, for example, a p-type. The first and second semiconductors 44 and 46, respectively, need to have different electron densities for the Peltier effect to work.

In some embodiments the top plate 34 and/or bottom plate 36 can be used as electrodes (e.g., to determine a position, etc.) when not being used as part of the operation of the TEC. The top plate 34 and/or bottom plate 36 can alternate between being used as electrodes and TECs. For example, energy can be driven to the top plate 34 and/or bottom plate 36 as electrodes, then the energy delivery (e.g., application of or removal of energy) can be stopped, and the electrodes can then be used to listen or detect signals (e.g., detect to see if treatment is effective). The top plate 34 and/or bottom plate 36 can be used to ablate and listen, which can provide for, for example, active feedback. In some embodiments, the listening stage can be considered a diagnostic mode.

The first semiconductor 44 and the second semiconductor 46 can be connected thermally in parallel and electrically in series. The first semiconductor 44 and the second semiconductor 46 can be connected, for example, with a connector plate 48. The connector plate 48 can connect the first semiconductor 44 and the second semiconductor 46 (e.g., adjacent first semiconductor 44 and second semiconductor 46). When a direct current (DC) voltage is applied across the plurality of semiconductors 38 there is a flow of DC current across a junction between the plurality of semiconductors 38 which causes a temperature difference.

The side of the TEC 32 with a cooling plate absorbs heat which is then transferred to a heating plate on the opposite side of the TEC. The top plate 34 and the bottom plate 36 can be either the cooling plate or the heating plate (e.g., if the top plate 34 is the heating plate, the bottom plate 36 is the cooling plate and if the top plate 34 is the cooling plate the bottom plate 36 is the heating plate).

Figure 3:
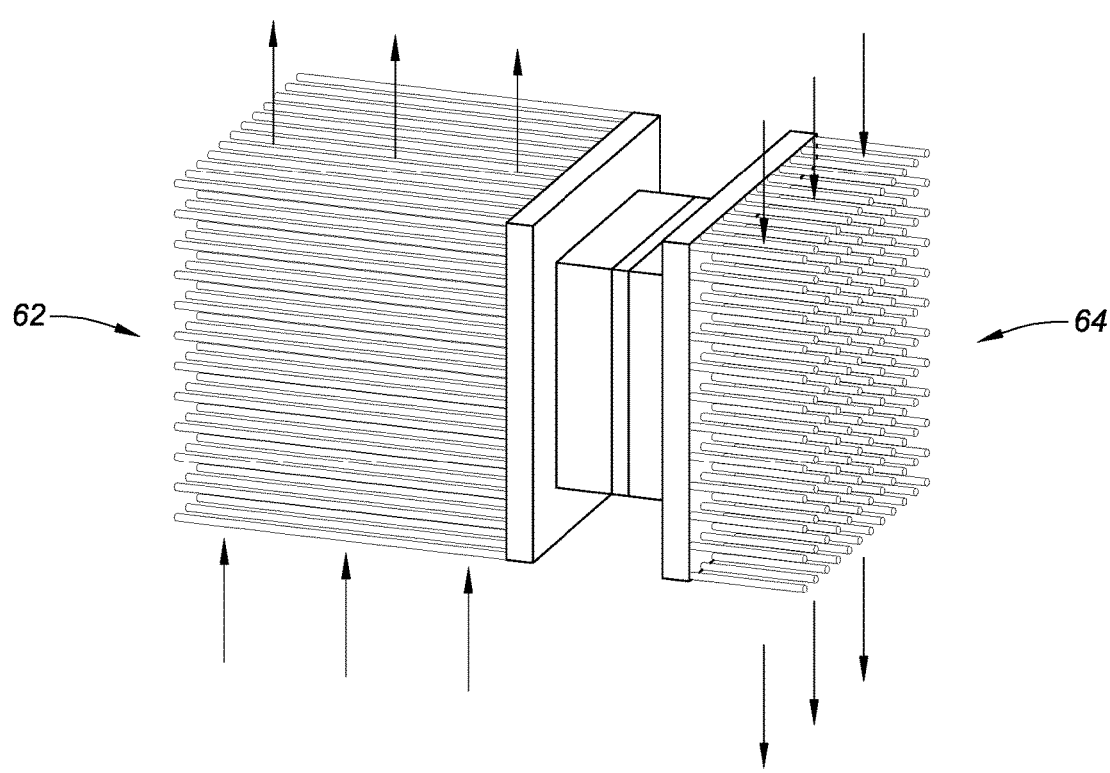
FIG. 3 is a isometric view of an exemplary heat flux flow model, in accordance with embodiments of the present disclosure.

FIG. 3 is a schematic view of an exemplary heat flux flow model, in accordance with embodiments of the present disclosure. The exemplary heat flux flow model 60 includes a hot side 62 and a cold side 64. Arrows representing an exemplary flow of heat (e.g., out of the hot side 62 and into the cold side 64) are shown. A single-stage TEC can typically produce a maximum temperature difference of 70° C. between the heating plate and the cooling plate. The amount of heat that can be absorbed is proportional to the current (or voltage) flowing through the TEC and time.

$$W = P*I*t$$

Where P is the Peltier Coefficient, I is the current, and t is the time. The Peltier Coefficient is dependent on temperature and the materials used in the TEC.

Figure 4:
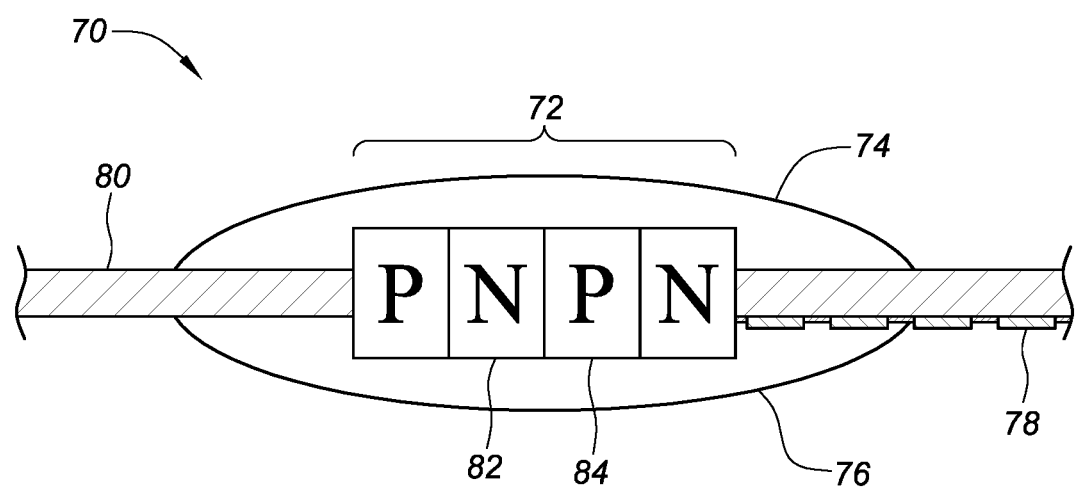
FIG. 4 shows an isometric side and top view of a thermoelectric element, in accordance with embodiments of the present disclosure.

FIG. 4 shows a side view of a thermoelectric element, in accordance with embodiments of the present disclosure. The thermoelectric element 70 can include a plurality of semiconductors 72, a first conductive surface 74, a second conductive surface 76, a conductive trace 78 and a flexible substrate (e.g., a thin film, a support structure, a membrane, a braid or a lattice) 80. The plurality of semiconductors 72 can include n-type 82 and p-type semiconductors 84. The first conductive surface 74 and the second conductive surface 76 can be made from any suitable conductive material (e.g., a conductive polymer or a metal). The first conductive surface 74 and the second conductive surface 76 can be the same material or they can be different materials. The conductive trace 78 can include one or more conductive paths to electrically connect a plurality of thermoelectric elements 70 to a power supply or a controller (e.g., an ECU). In other embodiments multiple conductive traces 78 can connect the each thermoelectric elements 70. The plurality of thermoelectric elements 70 can be electrically connected in series or in parallel.

Figure 5:
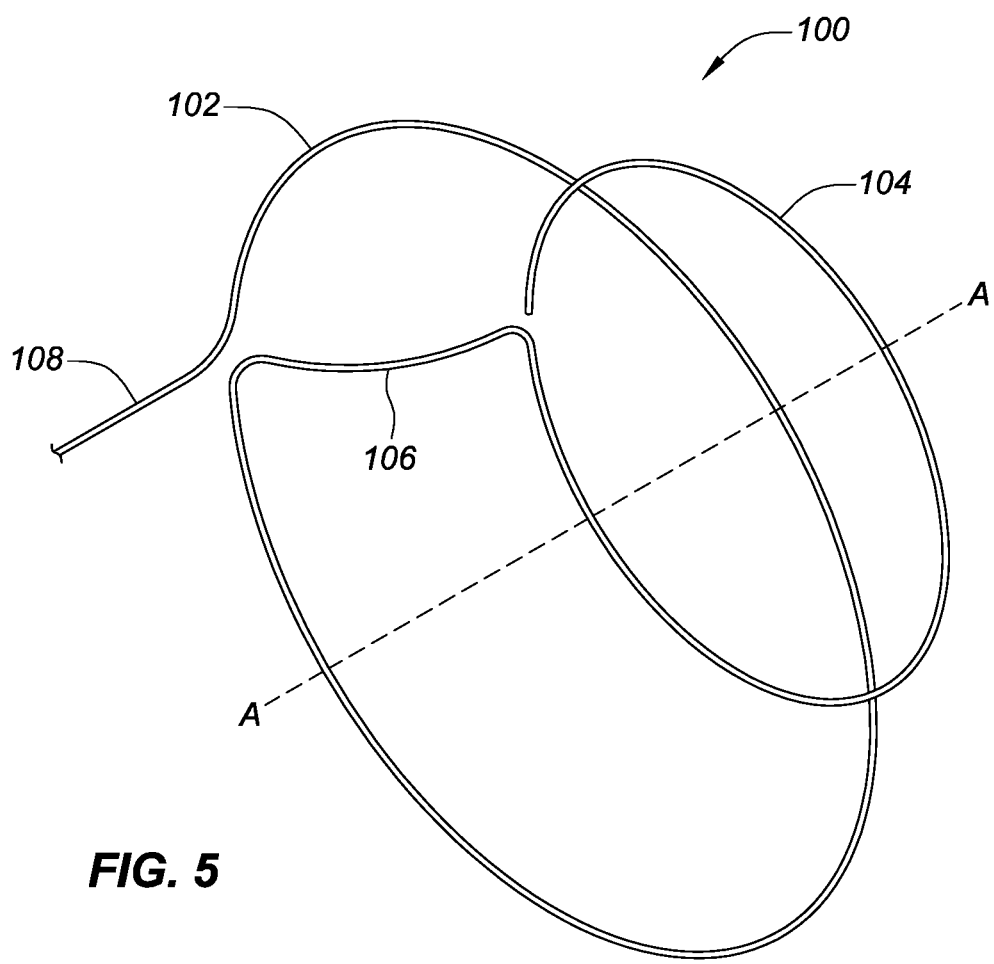
FIG. 5 is an isometric side and distal end view of a flexible catheter structure that can include that can include an alternative shaping element comprising, a plurality of shaping hoops that are connected in this embodiment, where the plurality of shaping hoops comprises a first or proximal shaping hoop and a second or distal shaping hoop, in accordance with embodiments of the present disclosure.

FIG. 5 is an isometric side and distal end view of a flexible catheter structure that can include that can include an alternative shaping element comprising, a plurality of shaping hoops that are connected in this embodiment, where the plurality of shaping hoops comprises a first or proximal shaping hoop and a second or distal shaping hoop, in accordance with embodiments of the present disclosure. A shaping element 100 can include a first shaping hoop (or proximal shaping hoop) 102 and a second shaping hoop (or distal shaping hoop) 104. In other embodiments, the first shaping hoop 102 and the second shaping hoop 104 can be separate elongate elements (not shown). Additional shaping hoops can be used to change the profile of the shape created (e.g., a third shaping hoop, and/or a fourth shaping hoop (not shown) could be added). The shaping element 100 can be used as a support structure for an anatomically configured device (also discussed with respect to FIG. 6, below). As described herein, the additional shaping hoops can similarly be connected to, for example, one or more pull wires or other similar devices that allow manipulation of the shaping hoops (e.g., longitudinal movement of the shaping hoops, changing the shape of the shaping hoops, etc.).

The first shaping hoop 102 can have a larger radius than the second shaping hoop 104 and can be located proximally with respect to the second shaping hoop 104. A hoop interconnective section 106 can connect the first and second shaping hoops 102 and 104. The hoop interconnective section 106 can be any suitable length to achieve the desired space between the first and second shaping hoops 102 and 104, respectively. The hoop interconnective section 106 can be shaped to fit a contour of the tissue (e.g., a single curve, multiple curves, etc.). The first shaping hoop 102 can be connected to a connecting section 108 that can be connected to pull wires or other similar devices to facilitate deployment of the shaping element 100 that forms the first shaping hoop 102 and second shaping hoop 104 at various locations in a body 16 (e.g., the heart).

In some embodiments, the first and second shaping hoops 102 and 104 can include a plurality of interactive elements (not shown). The plurality of interactive elements can be mounted on the first and second shaping hoops 102 and 104 using any suitable method (e.g., adhesive, etc.). The plurality of interactive elements can be connected with a plurality of conductive electrical traces. The conductive electrical traces can be electrically connected (e.g., a plurality of conductive electrical traces, wires, etc.) to a power supply, controller, medical positioning system 14 or other device used to generate a signal.

Figure 6:
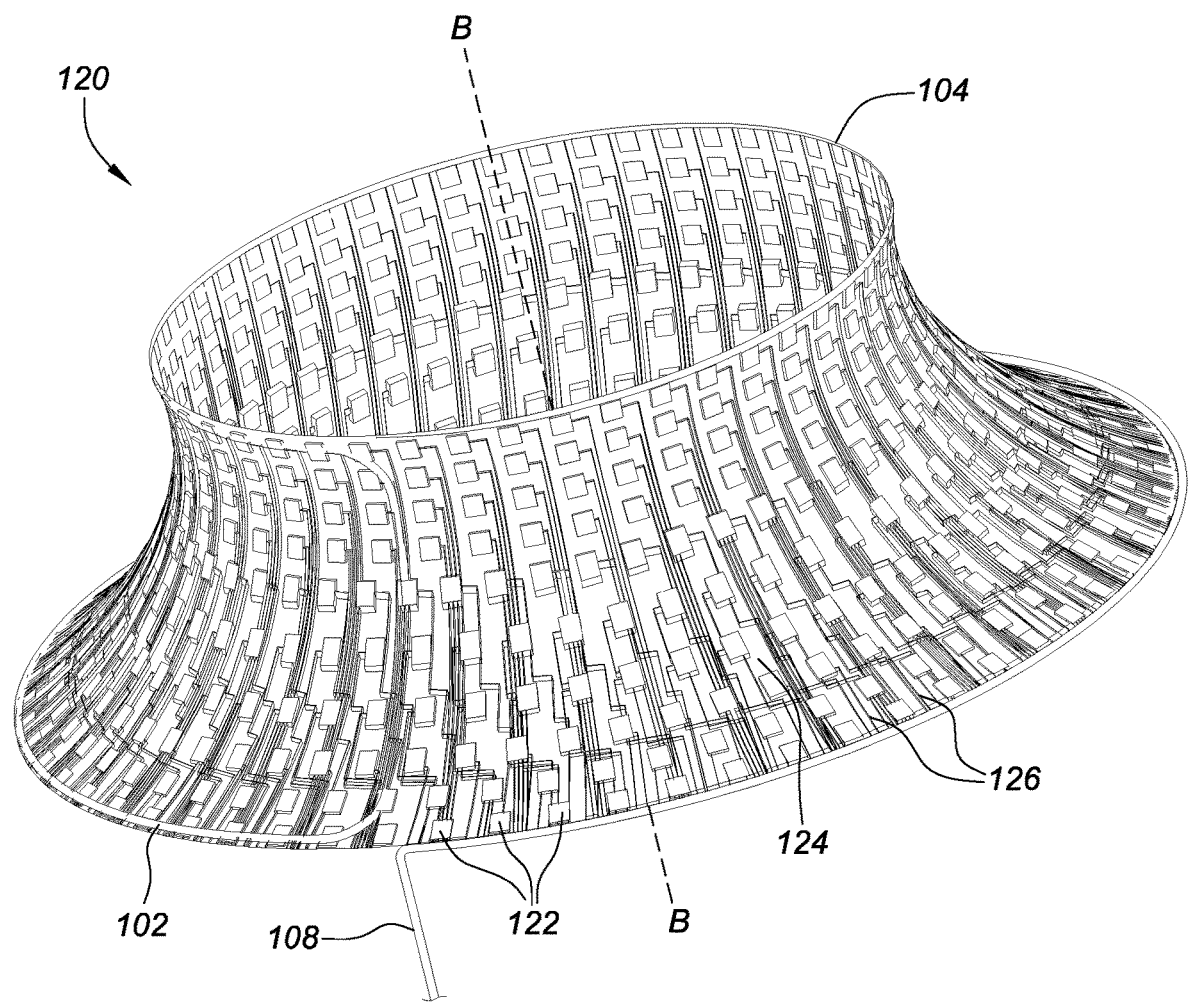
FIG. 6 is an isometric side and distal end view of a flexible catheter structure comprising an anatomically configured device that includes the first shaping hoop and the second shaping hoop of FIG. 5, in accordance with embodiments of the present disclosure.

FIG. 6 is an isometric side and distal end view of a flexible catheter structure comprising an anatomically configured device that includes the first shaping hoop and the second shaping hoop of FIG. 5, in accordance with embodiments of the present disclosure. The tissue shaping device 120 can include a plurality of thermoelectric elements 122 and a support structure 124 (e.g., a thin film, a flexible substrate, a membrane, a braid or a lattice) at, for example, the distal end portion 26 of shaft 22. The plurality of thermoelectric elements 122 can be electrically connected, for example, with a plurality of conductive traces 126, to an ECU or other signal generator. The support structure 124 can include struts made of any suitable materials (e.g., Nitinol) that permit expansion/contraction of the support structure 124 to facilitate locating the tissue shaping device 120 to a site in the patient's body 16.

The tissue shaping device 120 can include the first shaping hoop 102 and the second shaping hoop 104 referenced in FIG. 5. The first shaping hoop 102 and the second shaping hoop 104 may be formed from a single elongate element (e.g., a wire or other structure) or more than one elongate element (e.g., the first shaping hoop is one elongate element and the second shaping hoop is a second elongate element). Additional shaping hoops can be used to change the profile of the shape created (e.g., a third shaping hoop could be added (not shown)).

The first shaping hoop 102 second shaping hoop 104 can be aligned so that each is centered on an axis defined by the line BB. The first shaping hoop 102 and second shaping hoop 104 may can be formed by any suitable method including pre-formed heat set shapes. The first shaping hoop 102 and second shaping hoop 104 can be formed from wire or polymer or other suitable material. The material used for the first shaping hoop 102 and second shaping hoop 104 should be sufficiently rigid to "re-model" PV or other anatomical location. The sizes (e.g., the diameter of the first shaping hoop 102 and the second shaping hoop 104 can be specified so that they are slightly larger than the anticipated diameter of the corresponding location in the PV or other anatomical location). For example, the re-modeling of the PV occurs when the PV temporarily takes the shape of the first shaping hoop 102 and second shaping hoop 104.

In some embodiments, the first shaping hoop can be sized to be wider than an opening of the PV (not shown). For example, the first shaping hoop can be larger than the embodiment shown with the shaping hoop 102, allowing the first shaping hoop to contact tissue proximate the PV opening (e.g., resting against an antral wall). In some embodiments, the second shaping hoop can be sized to fit into various locations of the PV. For example, with a larger first shaping hoop as described above the second shaping hoop can be sized similar to the first shaping hoop 102 shown in FIG. 6, or smaller than the second shaping hoop 104 shown in FIG. 6 (e.g., to all the second shaping hoop to fit into smaller portions of the PV and/or other locations).

The variations in hoop size described above can allow the flexible substrate 146 to contact various portions of tissue. For example, in embodiments where the first shaping hoop is be larger than the embodiment shown with the shaping hoop 122 in FIG. 9B, the flexible substrate 146 can contact tissue of an antral wall proximate the PV. The flexible structure (e.g., flexible substrate 124) can conform to a contour of the tissue allowing contact between the plurality of thermoelectric elements (e.g., thermoelectric elements 122) and/or other sensors coupled with the flexible substrate. With the larger first shaping hoop, mapping and/or therapy (e.g., ablation of tissue, cooling/heating of tissue) can be applied at any point between the first and the second shaping hoops (e.g., from areas proximate the PV opening to areas into the PV).

In some embodiments, the tissue shaping device 120 can include a plurality of thermoelectric elements 122 and it can also include a plurality of temperature sensors. The plurality of temperature sensors can be combined with the plurality of thermoelectric elements 122 (e.g., each thermoelectric element can have a temperature sensor next to it) or located near the plurality of thermoelectric elements 122 (e.g., the temperature sensors can alternate between the thermoelectric elements). The temperature sensors can, for example, correspond in number to the plurality of thermoelectric elements 122 or the number can differ. Each of the plurality of temperature sensors can be proximate one or more of the plurality of thermoelectric elements 122. Each of the plurality of temperature sensors and the plurality of thermoelectric elements 122 can be selectively activated.

In other embodiments, additional sensors can be included on the tissue shaping device 120. For example, sensors can be included that have a single function (e.g. measuring temperature, contact force, total force, strain, position, biological factors, chemical (e.g., capable of delivery and/or monitoring of drugs/chemical, etc.), light-emitting acoustic, ultrasound, energy receiving and/or measuring diagnostic, etc.) or multiple functions. As described herein, the sensors can allow for various treatment and/or therapy (e.g., ablation) or data gathering (e.g. measuring temperature, contact force, total force, strain, position, etc.).

The plurality of temperature sensors can measure temperature data about the heating or cooling being done by the plurality of thermoelectric elements 122. For example, the plurality of temperature sensors can determine a first temperature of tissue at an ablation site and a second temperature at a site proximate the ablation site. The plurality of temperature sensors can also determine a temperature of a fluid (e.g., blood) proximate the ablation site where the fluid is in contact with the plurality of temperature sensors.

As shown in FIG. 6, each of a plurality of thermoelectric elements 122 can be a thermoelectric element that uses the Peltier effect to heat or cool tissue or fluid in a patient. For example, the plurality of thermoelectric elements 122 can be used to reduce the temperature of the fluid (e.g., blood) or tissue. The number of thermoelectric elements 122 can vary. FIG. 6 shows the plurality of thermoelectric elements 122 equally spaced covering the entire area between the first shaping hoop 102 and second shaping hoop 104. The spacing between the plurality of thermoelectric elements 122 can be varied (e.g., a similar density of thermoelectric elements or a different or variable density of thermoelectric elements). For example, the thermoelectric elements nearest the first shaping hoop 102 (e.g., the larger diameter) can be closer to each other compared to the thermoelectric elements nearest the second shaping hoop 104 (e.g., the smaller diameter). In some embodiments, the thermoelectric elements can be arranged in various lines or other configurations to facilitate heating or cooling in specific locations relative to the placement of the first and second shaping hoops 102 and 104 in the body 16 (e.g., the heart).

An embodiment of FIG. 6, can have, for example, the first shaping hoop 102 with a diameter of 18 mm and the second shaping hoop 104 with a diameter of 28.5 mm. The distance between the first shaping hoop 102 and second shaping hoop 104 can be 7.5 mm (measured along an axis parallel to the line BB). In some embodiments, the thermoelectric elements 122 can be 0.5 mm per side (square configuration). The conductive traces 126 can be, for example, 0.01 mm in thickness. Other suitable sizes for the thermoelectric elements 122 can be used. The tissue shaping device 120 can be deployed or delivered using a deflectable catheter or a guidewire based delivery or other delivery method.

Figure 7:
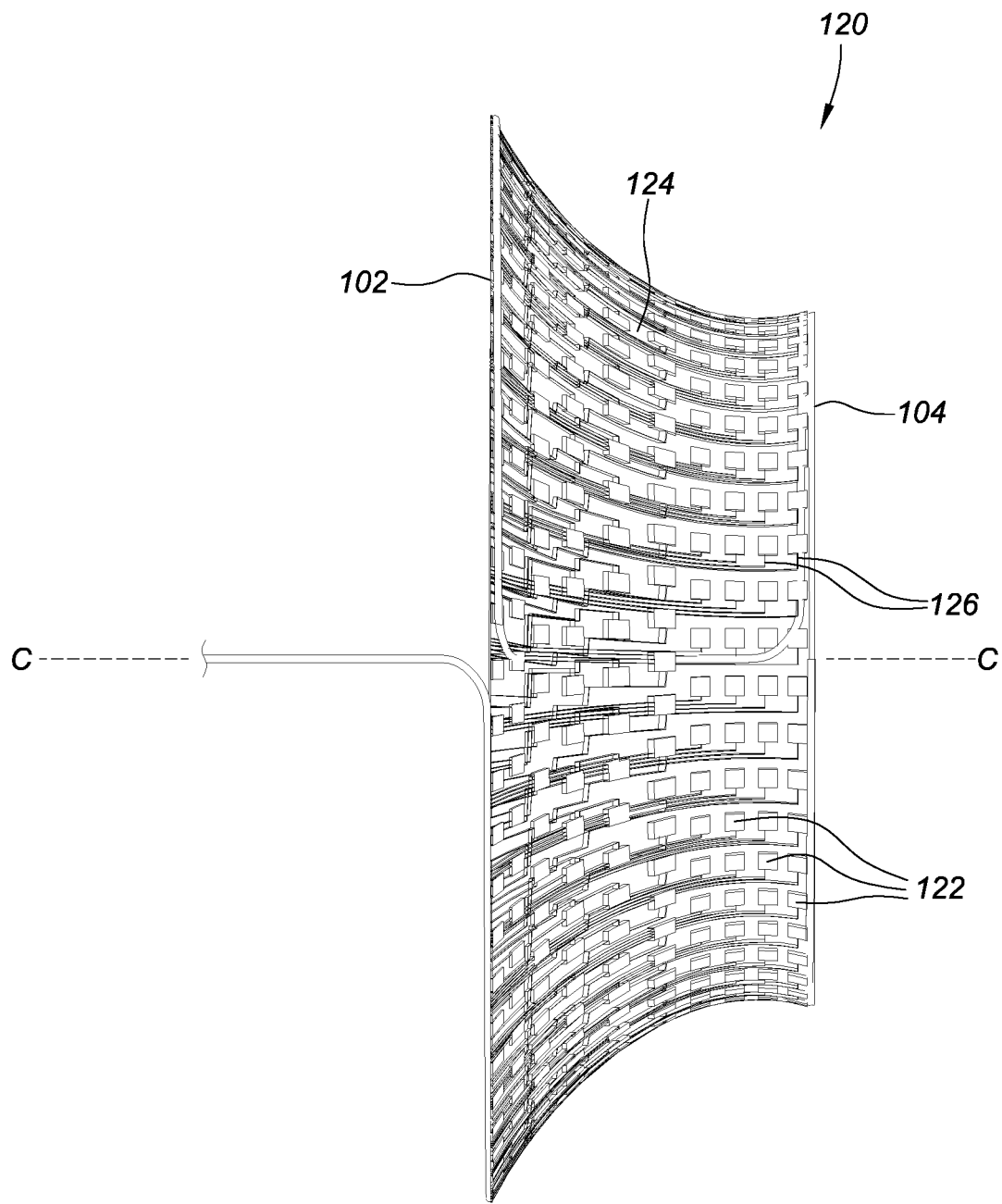
FIG. 7 is an isometric side view of the flexible catheter structure comprising the anatomically configured device that includes the first shaping hoop and the second shaping hoop of FIG. 6, in accordance with embodiments of the present disclosure.

FIG. 7 is an isometric side view of the flexible catheter structure comprising the anatomically configured device that includes the first shaping hoop and the second shaping hoop of FIG. 6, in accordance with embodiments of the present disclosure. As described above in FIG. 6 above, an tissue shaping device 120 can be used to form a first shaping hoop 102 and a second shaping hoop 104. The flexible substrate 124 can be mounted between the first shaping hoop 102 and the second shaping hoop 104. The flexible substrate 124 can have a plurality of thermoelectric elements 122 mounted to it. The plurality of thermoelectric elements 122 can be connected to a power supply, controller, medical positioning system 14 or other device used to generate a signal.

The flexible substrate 124 can be mounted between the first and second shaping hoops 102 and 104. The flexible substrate 124 can have a plurality of thermoelectric elements 122 mounted to it. The plurality of thermoelectric elements 122 can be connected to a plurality of conductive electrical traces 126. The plurality of conductive electrical traces 126 can be connected to a power supply, controller, medical positioning system or other device used to generate a signal.

In an embodiment shown in FIG. 7, the anatomically configured device can be shaped, to fit a location proximal the PV. For example, FIG. 7 shows the first shaping hoop 102 and the second shaping hoop 104 where each can be sized to fit into a location of the PV (e.g., the first shaping hoop 102 can fit a location more proximal in the opening of the PV (e.g., more antral) and the second shaping hoop 104 can fit a location more distal in the PV (e.g., more ostial). The flexible substrate 124 can be flared or curved between the first shaping hoop 102 and the second shaping hoop 104 to approximately match the corresponding contour or shape of the PV where the first shaping hoop 102 and the second shaping hoop 104 are placed.

As shown in the embodiment depicted in FIG. 7, the plurality of thermoelectric elements 122 can be located on the flexible substrate 124. The plurality of thermoelectric elements 122 can be arranged, for example, in a pattern with equal spacing between all of the thermoelectric elements 122. In other embodiments, the thermoelectric elements 122 can have varying spacing (e.g., closer spacing near the first shaping hoop 102 and farther spacing near the second shaping hoop 104).

Figure 8:
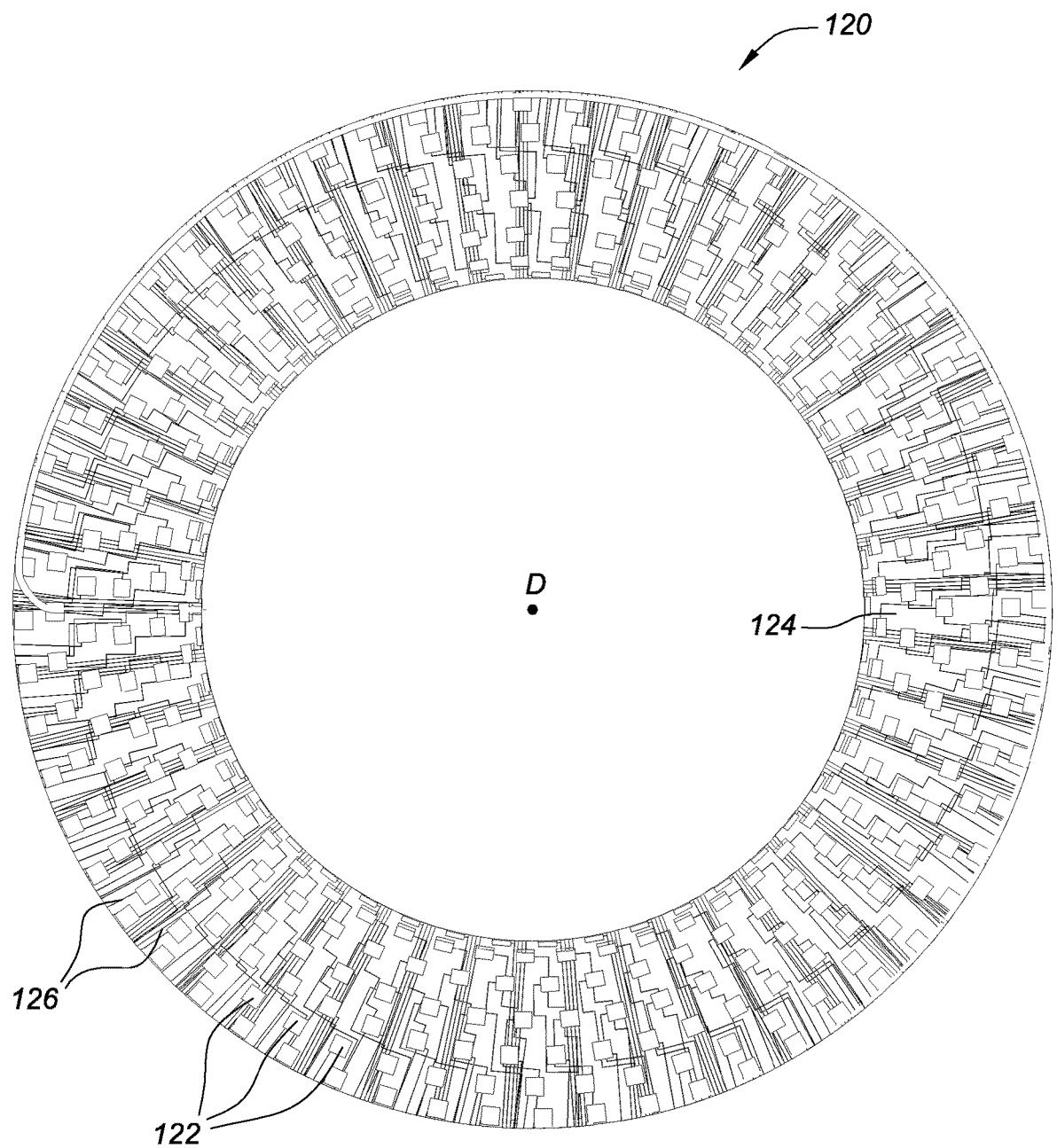
FIG. 8 is a proximal end view of the flexible catheter structure comprising the anatomically configured device of FIGS. 6 and 7, in accordance with embodiments of the present disclosure.

FIG. 8 is a proximal end view of the flexible catheter structure comprising the anatomically configured device of FIGS. 6 and 7, in accordance with embodiments of the present disclosure. The anatomically configured device can include the first shaping hoop 102 and the second shaping hoop 104, and the support structure 124 are centered on an axis defined by the line D (shown here as a single point as the axis is perpendicular to the surface of the paper with the drawing). The support structure 124 can be, for example, a flexible substrate, a braided material, a lattice, or a web.

The support structure 124 can also be shaped to extend between the first shaping hoop 102 and second shaping hoop 104 when they are aligned with an axis defined by the line D. For example, the support structure 124 can have a generally conical shape and/or flared conical shape with a curved surface that supports a plurality of thermoelectric elements 122 to facilitate contact between the thermoelectric elements 122 and tissue (e.g., locations proximate the PV). The thermoelectric elements 122 are further described herein. In some embodiments, the support structure 124 can also have, for example, a plurality of sensors (not shown) that have a single function (e.g. measuring temperature, contact force, total force, strain, position, etc.). As described herein, contact between the thermoelectric elements 122 and the plurality of sensors can allow for various treatment (e.g., ablation) or data gathering (e.g. measuring temperature, contact force, total force, strain, position, etc.). In various embodiments, each of the plurality of sensors can be selectively activated. For example, a single sensor can be activated for ablation, a different sensor can be activated for data gathering/diagnostics and another sensor can be activated to measure temperature.

The re-modeling of the PV when the first shaping hoop 102 and second shaping hoop 104 are in contact with the PV can cause the PV tissue to be in contact with a plurality of the thermoelectric elements 122 located on the first shaping hoop 102 and second shaping hoop 104 (or on the support structure 124 with other sensors). The thermoelectric elements 122 can allow for, for example, cooling and/or heating to both antrum and ostium/sleeve of the PV. The plurality of thermoelectric elements 122 provide sufficient distribution to cool a fluid (e.g., blood) or tissue proximate the plurality of thermoelectric elements 122 during a procedure such as, for example, ablation.

Figure 9:
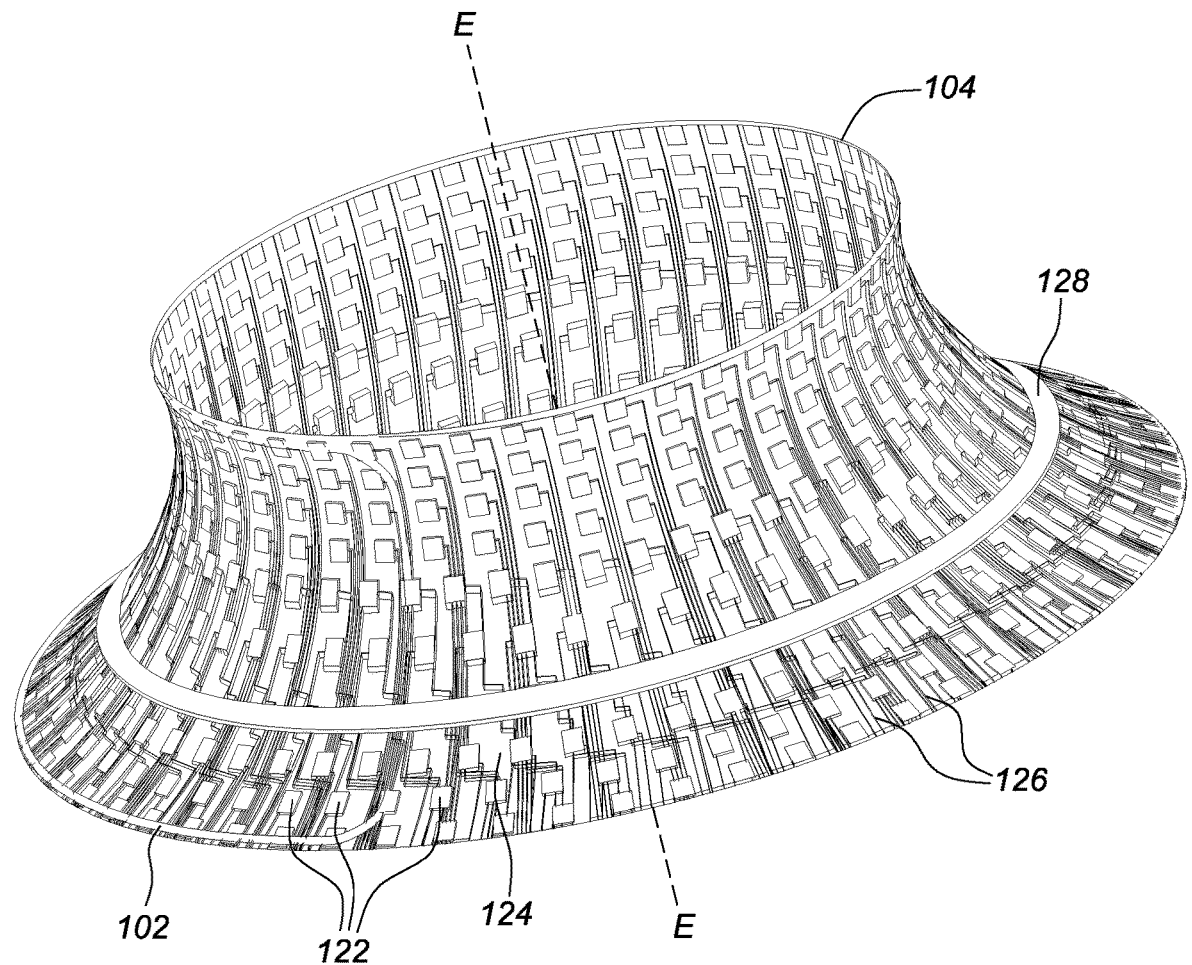
FIG. 9 is an isometric side and distal end view of a flexible catheter structure comprising an anatomically configured device, in accordance with embodiments of the present disclosure.

FIG. 9 is an isometric side and distal end view of a flexible catheter structure comprising an anatomically configured device, in accordance with embodiments of the present disclosure. In addition to a plurality of thermoelectric elements 122, a heat sink 128 can be included to add to the ability of the anatomically configured device to dissipate heat, in accordance with embodiments of the present disclosure. The heat sink 128 can be located, for example, between the first shaping hoop 102 and the second shaping hoop 104 and be, for example, circular in shape going around the entire circumference of the support structure 124 and generally parallel to the first shaping hoop 102 and the second shaping hoop 104. The heat sink 128 can be added between adjacent rows of thermoelectric elements 122 or the heat sink 128 can replace one of the rows of thermoelectric elements 122. More than one heat sink 128 can be included to achieve the desired cooling rate of, for example, the blood or the tissue. In other embodiments, the heat sink 128 can be located so it is generally parallel to an axis defined by the line EE (e.g., perpendicular the first shaping hoop 102 and the second shaping hoop 104). In some embodiments, where a thermoelectric element (or more than one) are being used to heat tissue, a cold sink can be included (instead of/in addition to a heat sink).

The heat sink 128 can be, for example, a single continuous strip of material or multiple strips of material. Other configurations of the heat sink 128 are possible to increase the surface area to allow for greater dissipation of heat (e.g., fins). The heat sink 128 can be made from any suitable material with a high thermal conductivity (e.g., metals such as copper, aluminum and its alloys).

Figure 10:
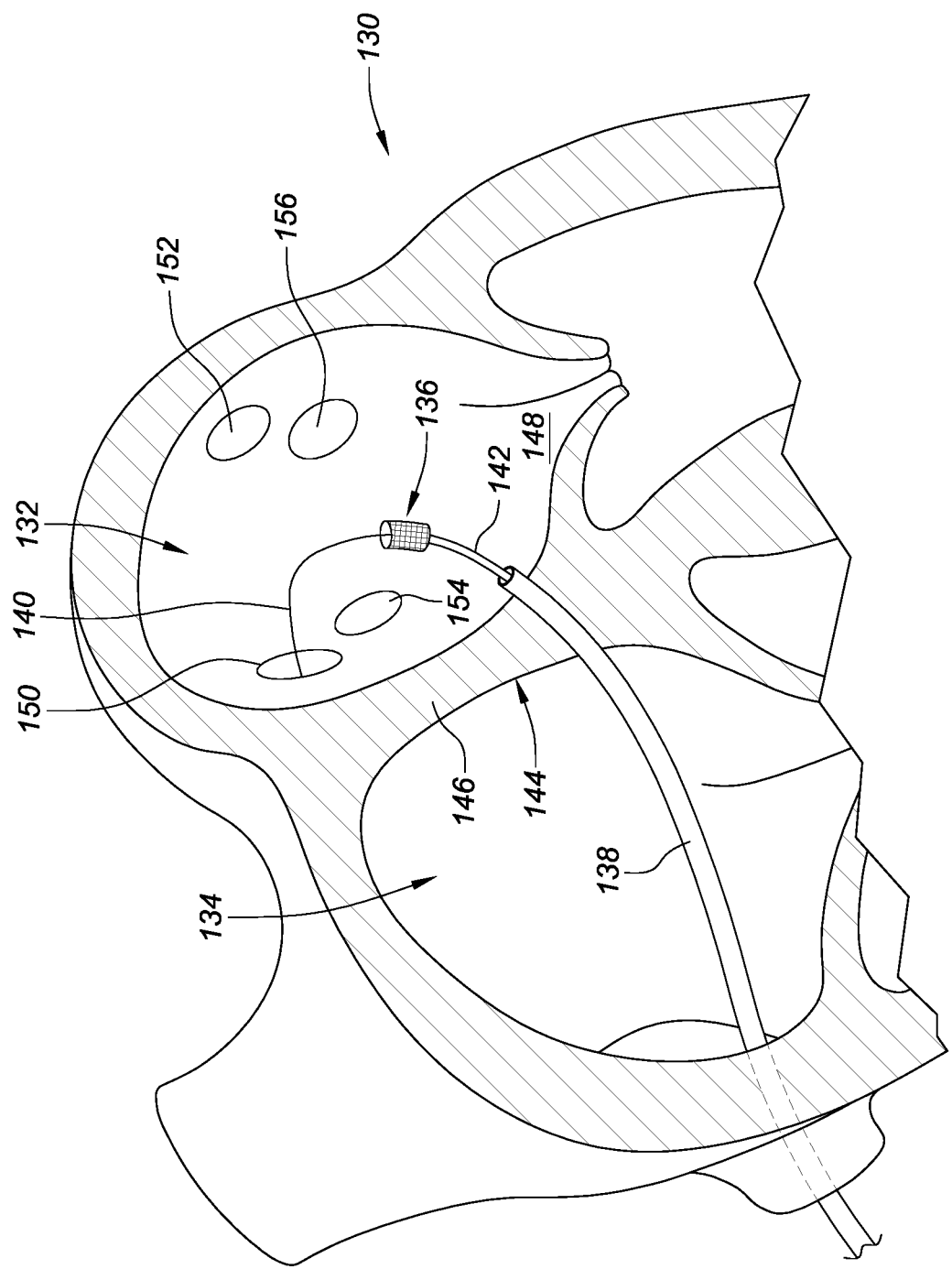
FIG. 10 is a cross-sectional front view of a portion of a heart with a flexible catheter structure comprising the anatomically configured device of FIGS. 6-8 about to be located in a pulmonary vein, consistent with various aspects of the present disclosure.

FIG. 10 is a cross-sectional front view of a portion of a heart with a flexible catheter structure comprising the anatomically configured device of FIGS. 6-8 about to be located in a pulmonary vein, consistent with various aspects of the present disclosure. As shown in FIG. 10, the heart 130 includes two upper chambers called the left atrium 132 and right atrium 134, and two lower chambers called the left ventricle and right ventricle (not shown).

As shown in FIG. 10, an anatomically configured device 136 may be introduced into the left atrium 132 by an introducer 138. A guide wire, 140 and a catheter 142 may guide the anatomically configured device 136 once introduced into the left atrium 132 by the introducer 138. Optionally, the anatomically configured device 136 may include positioning sensors (e.g., mapping electrodes, not shown) at one or more locations of the anatomically configured device 136 as described herein. In operation, the introducer 138 has its distal end positioned within the left atrium 132. As shown in FIG. 10, a transeptal approach may be utilized in which the introducer 138 is introduced through a peripheral vein (typically a femoral vein) and advanced to the right atrium 134. The introducer 138 makes a small incision into fossa ovalis 144 which allows the distal end of the introducer 138 to enter the left atrium 132 (through the transeptal wall 146) and to anchor itself to the wall of the fossa ovalis 144.

The anatomically configured device 136 may also be introduced into the left atrium 132 through the arterial system. In that case, the introducer 138 is introduced into an artery (such as a femoral artery) and advanced retrograde through the artery to the aorta, the aortic arch, and into the left ventricle. The anatomically configured device 136 is then extended from within a lumen of the introducer 138 to enter the left atrium 132 through mitral valve 148.

Once the introducer 138 is in position within the left atrium 132, the anatomically configured device 136 is advanced out a distal end of the introducer 138 and toward one of the pulmonary veins (e.g., 150, 152, 154, and 156). In FIG. 10, the target pulmonary vein is right superior pulmonary vein 150. A first steerable portion 140 and a second steerable portion 142 of the catheter are manipulated until the distal end of the anatomically configured device 136 is directed toward the ostium of the target pulmonary vein, after the anatomically configured device 136 is extended into the pulmonary vein (e.g., superior pulmonary vein 150).

Carried near a distal end of the catheter 142, the anatomically configured device 136 can remain in a collapsed condition so that it may pass through introducer 138, and enter target pulmonary vein 150. Once in position, the anatomically configured device 136 can be deployed (e.g., expanded), so that it engages and secures the anatomically configured device 136 in a position axial to the target pulmonary vein 150 and in contact with tissue of the pulmonary vein 150.

The embodiment of FIG. 10 may include mapping electrodes (not shown). The mapping electrodes may be ring electrodes that allow the clinician to perform a pre-deployment electrical mapping of the conduction potentials of the pulmonary vein 150. Although the anatomically configured device 136 can include electrodes or sensors used for mapping, mapping electrodes or sensors may alternatively be carried on-board a separate electrophysiology catheter (not shown).

Figure 11:
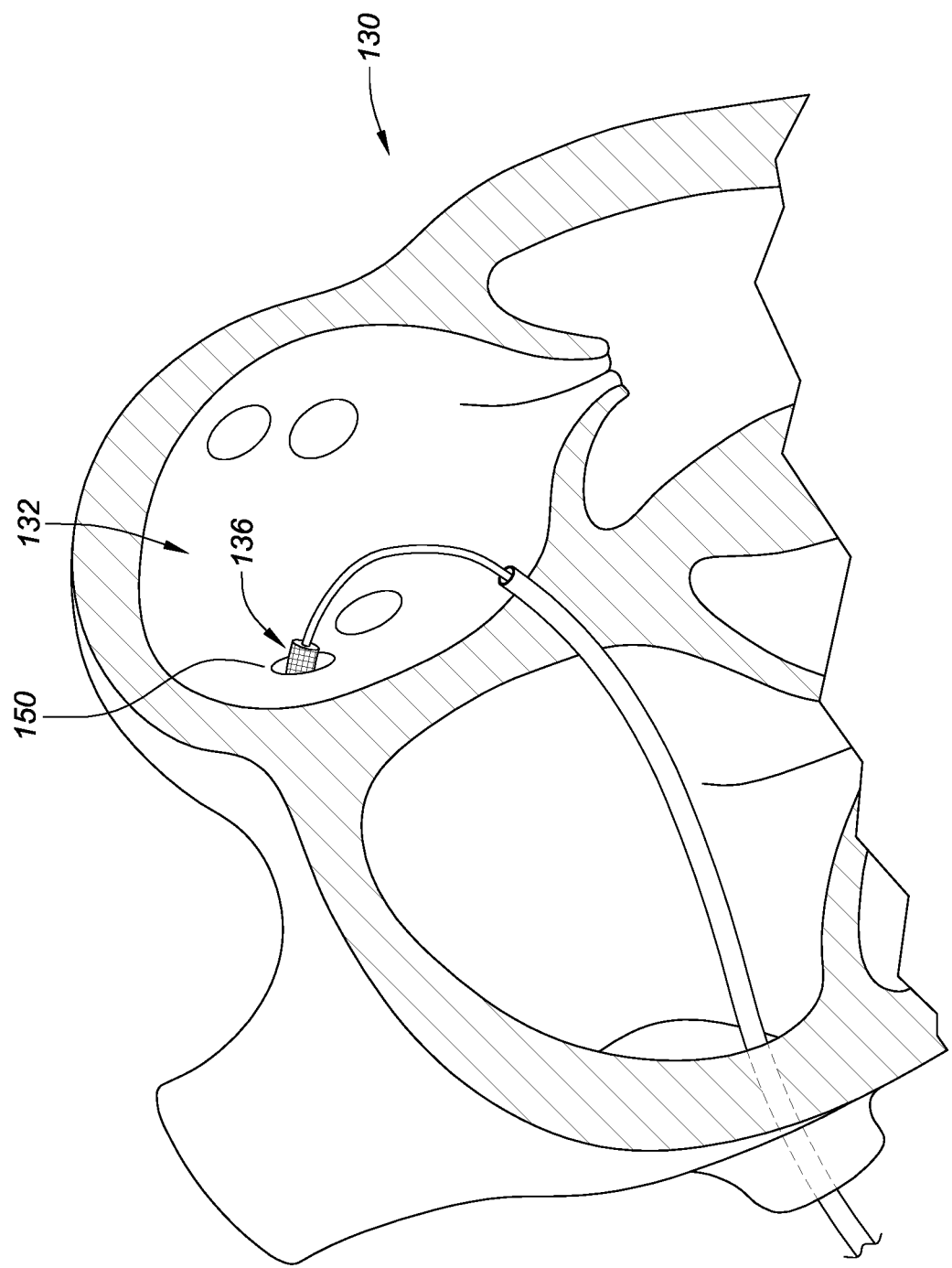
FIG. 11 is a cross-sectional front-view of a left atrium with the catheter with the anatomically configured device of FIG. 10 positioned within a pulmonary vein, prior to deployment, consistent with various aspects of the present disclosure.

FIG. 11 is a cross-sectional front view of a heart with the flexible catheter structure comprising the anatomically configured device of FIGS. 6-8 positioned within the right superior pulmonary vein, prior to deployment of the anatomically configured device, consistent with various aspects of the present disclosure.

FIG. 11 shows anatomically configured device 136 advanced into the ostium of pulmonary vein 150. As the anatomically configured device 136 enters the pulmonary vein 150, mapping may be conducted using position sensors/ electrodes (not shown) in order to verify proper location prior to deployment of the anatomically configured device 136.

Aspects of the present disclosure can improve the fit of the anatomically configured device 136 within the pulmonary vein 150 with an anatomically configured device profile that betters conforms to the contours of the pulmonary vein 150 between antral and ostia portions thereof. This improved conformance between the expanded anatomically configured device 136 and pulmonary vein 150 can result in improved ablation therapy efficacy, and the reduced need for duplicative therapies.

In further example embodiments, the anatomically configured device 136 may be a specific to a particular pulmonary vein. For example, various studies have determined average, maximum, and minimum pulmonary vein diameters across various patient demographics. Using such data, anatomically configured devices for each of the pulmonary veins may be created and swapped out during a therapeutic procedure for atrial fibrillation patients, for example. Increasing efficacy of the ablation procedure. Various other parameters of a pulmonary vein may also be considered to tailor custom therapeutic solutions, thereby improving contact between each pulmonary vein and the anatomically configured device 136. In one specific example, where a range of diameters of a pulmonary vein ostia (e.g., right superior pulmonary vein) are between 15 and 20 millimeters, first portion of the anatomically configured device 136 may have a diameter around 19 millimeters to ensure contact (when inflated) between the pulmonary vein and the first portion for most patients, while limiting the potential for damage to smaller diameter pulmonary veins which may be permanently damaged by excess wall stress on the pulmonary vein tissue. Moreover, when the tissue is experiencing an excess wall stress, the ablation therapy can suffer from decreased efficacy and consistency of ablation.

Figure 12:
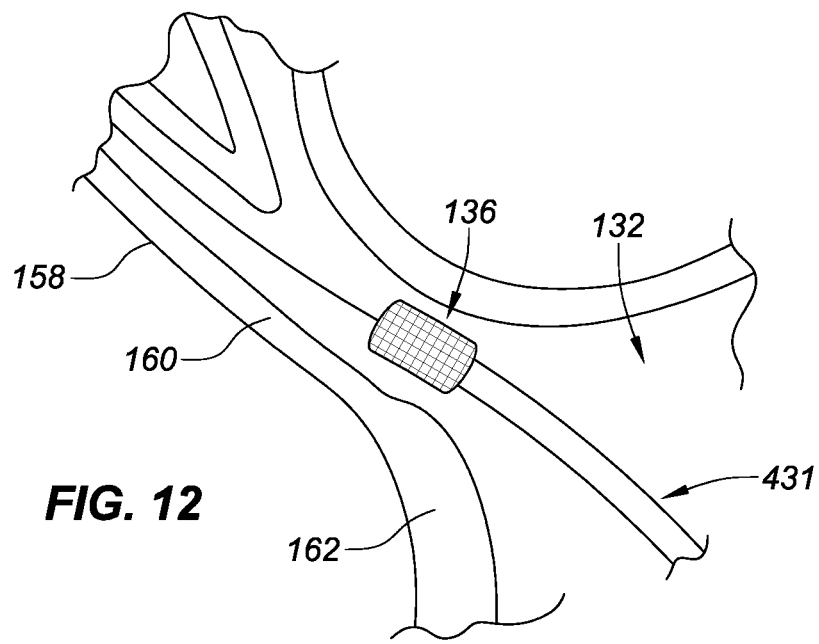
FIG. 12 is a cross-sectional front-view of a pulmonary vein with the anatomically configured device of FIGS. 6-9 positioned therein, prior to deployment of the anatomically configured device, consistent with various aspects of the present disclosure.

FIG. 12 is a cross-sectional front-view of a pulmonary vein with the anatomically configured device of FIGS. 6-9 positioned therein, prior to deployment of the anatomically configured device, consistent with various aspects of the present disclosure. FIG. 12 shows anatomically configured device 136 in position within target pulmonary vein 158 prior to deployment of the anatomically configured device 136. In one embodiment of the present disclosure, the proper location of the, anatomically configured device 136 may be determined/verified by mapping, prior to deployment of the anatomically configured device 136. As shown in FIG. 12, ostial and antral portions of the pulmonary vein, 160 and 162 respectively, are irregular and varying in shape along both a longitudinal length and a cross-section of the pulmonary vein. Importantly, it has been discovered that many pulmonary veins exhibit an oval cross-sectional shape, as opposed to circular. Accordingly, where embodiments of the anatomically configured device 136 can be substantially circular, during expansion certain portions of the oval cross-sectional shape of the pulmonary vein may be overly stressed, while other portions of the pulmonary vein do not contact the anatomically configured device limiting, for example, efficacy of the ablation therapy. Accordingly, aspects of the present disclosure are directed to an anatomically configured device with a substantially oval shape. Such embodiments minimize and unify wall stress along a circumference of the pulmonary vein tissue.

Figure 13:
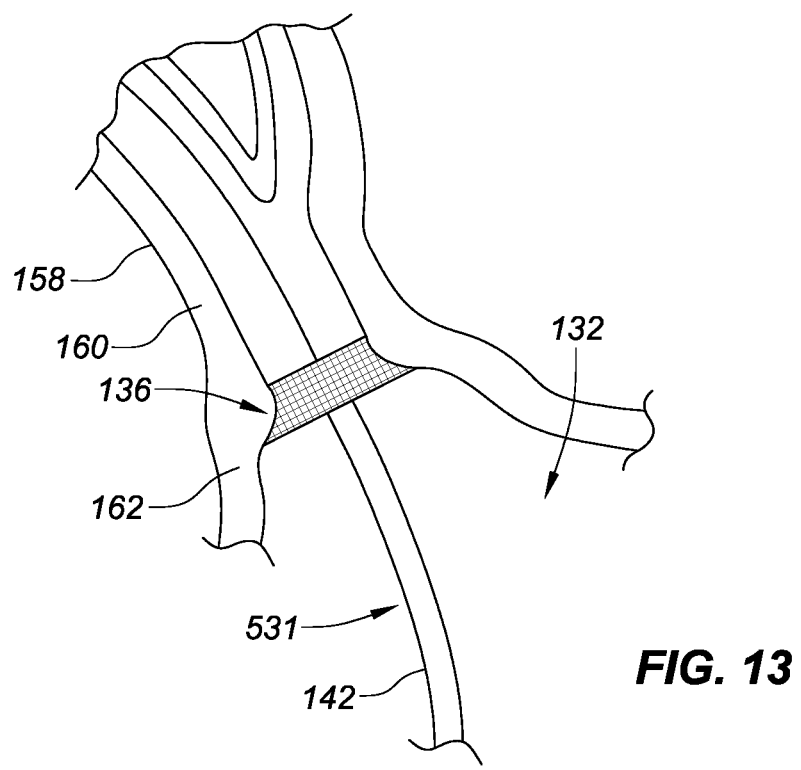
FIG. 13 is a cross-sectional front-view of a pulmonary vein with the anatomically configured device of FIGS. 6-9 deployed therein, consistent with various aspects of the present disclosure.

FIG. 13 is a cross-sectional front-view of a pulmonary vein with the anatomically configured device of FIGS. 6-9 deployed therein, consistent with various aspects of the present disclosure. FIG. 13 shows expanded anatomically configured device 136 engaged between the ostial portion 160 and the antral portion 162 of the target pulmonary vein 158. In its expanded state shown in FIG. 13, anatomically configured device 136 engages inner walls of target pulmonary vein 158. The expanded shape of the anatomically configured device 136 can have distinct portions, designed to more precisely match the contours of the pulmonary vein. This distinct shape can increase the surface area contact between the pulmonary vein and the expanded anatomically configured device 136, which can improve, for example, the efficacy of an ablation therapy or other therapy that relies on surface contact between the anatomically configured device 136 and pulmonary vein tissue. Without continuous contact along a circumference of the pulmonary vein, a continuous lesion along the circumference may not be formed or, for other sensors, data may not be accurate or possible.

Once therapy (e.g., ablation, tissue cooling, etc.) is complete, anatomically configured device 136 may be contracted and then retracted back into introducer 138. An electrophysiology catheter, or electrodes/sensors proximal and distal to the anatomically configured device 136, may be used to verify the efficacy of the therapy prior to removal of the anatomically configured device 136. In various embodiments of the present disclosure, and described herein, additional electrodes/sensors may also be positioned on the anatomically configured device 136, either alone, or in conjunction with the other sensors.

Other structures or configurations are possible to facilitate locating and using the elements and structures described above. U.S. Provisional Patent Application No. 62/5221, 992, titled "Apparatuses and Methods for Delivering and Sensing Multiple Cardiac Ablations," and U.S. Provisional Patent Application No. 62/521,990, "Apparatuses and Methods for Delivering Multiple Cardiac Ablations,", both filed concurrently, are herein incorporated by reference in their entirety.

Although at least one embodiment of an apparatus and method for cooling tissue has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the spirit of the disclosure as defined in the appended claims.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An apparatus for cooling a tissue or a fluid, comprising:
an elongate shaft extending along a longitudinal axis and comprising a proximal portion and a distal portion;
a support structure located at the distal portion, wherein the support structure is expandable from a contracted state to an expanded state, and wherein the support structure has a flared conical shape with a curved surface; and
a thermoelectric element, wherein the thermoelectric element is located on the curved surface of the support structure.

2. The apparatus of claim 1, further comprising a plurality of thermoelectric elements.

3. The apparatus of claim 2, wherein each of the plurality of thermoelectric elements further comprises:
a top plate;
a bottom plate;
a plurality of p-type semiconductors and a plurality of n-type semiconductors, wherein the plurality of p-type semiconductors and the plurality of n-type semiconductors are arranged in an alternating pattern and located between the top plate and the bottom plate; and
a plurality of connector plates, wherein the plurality of connector plates electrically connect adjacent pairs of the plurality of p-type semiconductors and the plurality of n-type semiconductors, wherein the plurality of p-type semiconductors and the plurality of n-type semiconductors are located on the support structure.

4. The apparatus of claim 2, wherein a number of the plurality of thermoelectric elements is greater at a distal portion of the flexible planar substrate compared to a proximal portion of the support structure.

5. The apparatus of claim 2, wherein a number of the plurality of thermoelectric elements is greater at a proximal location of the flexible planar substrate compared to a distal location of the flexible planar substrate.

6. The apparatus of claim 2, wherein the plurality of thermoelectric elements are electrically connected by a plurality of conductive traces to a power source.

7. The apparatus of claim 1, wherein the thermoelectric element comprises a Peltier device.

8. The apparatus of claim 1, wherein the support structure is formed from a shape memory material.

9. The apparatus of claim 1, further comprising a flexible planar substrate, wherein the flexible planar substrate is connected to the support structure and the thermoelectric element is located on the flexible planar substrate.

10. The apparatus of claim 9, wherein the flexible planar substrate is formed from a shape memory material.

11. The apparatus of claim 9, wherein the support structure is configured to cause a tissue to conform to the expanded state of the support structure.

12. The apparatus of claim 9, further comprising a heat sink strip, wherein the heat sink strip is located on the flexible planar substrate and wherein the heat sink strip comprises a material of high thermal conductivity.

13. An apparatus for cooling a tissue or a fluid for an elongate medical device comprising:
a first shaping hoop element configured to have an expanded state and a contracted state;
a second shaping hoop element located distally with respect to the first shaping hoop element and configured to have an expanded state and a contracted state, wherein each of the first and the second shaping hoop elements are transversely oriented when each is in the expanded state with respect to a longitudinal axis that extends through a center of each of the shaping hoop elements;
a support structure that extends between the first shaping hoop element and the second shaping hoop element; and
a thermoelectric element, wherein the thermoelectric element is located on the support structure.

14. The apparatus of claim 13, further comprising a plurality of thermoelectric elements.

15. The apparatus of claim 13, wherein the support structure is a braided material that extends between the first catheter end shape and the second catheter end shape.

16. The apparatus of claim 13, wherein the first shaping hoop element and the second shaping hoop element are formed from a single elongate.

17. The apparatus of claim 13, wherein the first shaping hoop element is formed from a first elongate element and the second shaping hoop element is formed from a second elongate element.

18. The apparatus of claim 13, further comprising a plurality of interactive elements, wherein the plurality of interactive elements comprise one or more of an energy delivery element, a thermocouple, a force sensor, a strain gauge, a position sensor, a strain sensor, a diagnostic element, a therapy element, a drug element, a chemical element, a biologic element, an acoustic element, an ultrasound element, a light-emitting element, a magnetic element, and a thermoelectric element.

19. The apparatus of claim 13, wherein the plurality of thermoelectric elements are electrically connected by a plurality of conductive traces, wherein the plurality of conductive traces are electrically connected to a power source.

20. The apparatus of claim 13, further comprising a heat sink strip, wherein the heat sink strip is located on the support structure and wherein the heat sink strip comprises a material of high thermal conductivity.

21. A system for cooling a tissue or a fluid, comprising:
a support structure having a flared conical shape with a curved surface;
a plurality of thermoelectric elements located on the curved surface;
an electronic control unit (ECU), wherein the ECU is configured to:
measure a first temperature at a location;
apply power to the plurality of thermoelectric elements; and
measure a second temperature at the location.

22. The system of claim 21, wherein each of the plurality of thermoelectric elements further comprise a plurality of p-type semiconductors, a plurality of n-type semiconductors, a top plate, and a bottom plate.

23. The system of claim 21, wherein the plurality of p-type semiconductors and the plurality of n-type semiconductors are electrically connected, in a pair, by a connector plate, wherein each pair comprises a single p-type semiconductor and a single n-type semiconductor.

24. The system of claim 21, further comprising a heat sink strip, wherein the heat sink strip and the plurality of thermoelectric elements are located on a flexible planar substrate and wherein the heat sink strip comprises a material of high thermal conductivity.

25. An apparatus for an elongate medical device comprising:
a flexible planar substrate having a flared conical shape with a curved surface;
a plurality of thermoelectric elements, wherein the plurality of thermoelectric elements are arranged in a first pattern on the curved surface of the flexible planar substrate; and
a plurality of interactive elements, wherein the interactive elements are arranged in a second pattern on the flexible planar substrate.

26. The apparatus of claim 25, wherein the first pattern of the plurality of interactive elements and the plurality of thermoelectric elements includes one of the plurality of interactive elements arranged in a plurality of longitudinal lines that extend from a distal end to a proximal end of the elongate medical device, the plurality of thermoelectric elements arranged in a plurality of longitudinal lines that extend from a distal end to a proximal end of the elongate medical device, a plurality of rows of interactive elements that are circumferentially disposed about an axis, a plurality of rows of thermoelectric elements that are circumferentially disposed about the axis and longitudinally spaced apart.

27. The apparatus of claim 25, wherein the plurality of thermoelectric elements and the plurality of interactive elements are electrically connected by a plurality of conductive traces, wherein the plurality of conductive traces are electrically connected to a power source.

28. The apparatus of claim 25, wherein the plurality of interactive elements further comprise one or more of an energy delivery element, a thermocouple, a diagnostic element, a therapy element, a drug element, a chemical element, a biologic element, an acoustic element, an ultrasound element, a light-emitting element, a magnetic element, and a thermoelectric element.

29. The apparatus of claim 25, wherein each of the plurality of thermoelectric elements further comprise a plurality of p-type semiconductors, a plurality of n-type semiconductors, a top plate, and a bottom plate.

* * * * *